United States Patent
Sugaya et al.

(10) Patent No.: US 8,152,979 B2
(45) Date of Patent: Apr. 10, 2012

(54) AMMONIA GAS SENSOR

(75) Inventors: Satoshi Sugaya, Aichi (JP); Hiroyuki Nishiyama, Aichi (JP); Wataru Matsutani, Aichi (JP); Shiro Kakimoto, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 325 days.

(21) Appl. No.: 12/170,824

(22) Filed: Jul. 10, 2008

(65) Prior Publication Data

US 2009/0014330 A1    Jan. 15, 2009

(30) Foreign Application Priority Data

Jul. 11, 2007 (JP) .................. 2007-181575
May 7, 2008 (JP) .................. 2008-120858

(51) Int. Cl.
*G01N 27/406* (2006.01)

(52) U.S. Cl. ........ 204/424; 204/425; 204/426; 204/427; 204/428; 204/429; 73/23.31; 73/23.32; 205/783.5; 205/785

(58) Field of Classification Search .......... 204/424–429; 205/783.5–785, 781; 73/23.31–23.32
See application file for complete search history.

(56) References Cited

U.S. PATENT DOCUMENTS

| | | | |
|---|---|---|---|
| 5,108,577 A * | 4/1992 | Mase et al. .................. 204/426 |
| 5,110,442 A * | 5/1992 | Kojima et al. ................ 204/426 |
| 6,767,442 B1 * | 7/2004 | Scheer et al. ................. 204/425 |
| 2003/0062264 A1* | 4/2003 | Kitanoya et al. .............. 204/424 |
| 2005/0139491 A1* | 6/2005 | Ohkuma ....................... 205/782 |
| 2005/0158458 A1* | 7/2005 | Sakai ............................ 427/123 |
| 2007/0080074 A1* | 4/2007 | Wang et al. ................. 205/780.5 |

* cited by examiner

*Primary Examiner* — Keith Hendricks
*Assistant Examiner* — Bach Dinh
(74) *Attorney, Agent, or Firm* — Sughrue Mion, PLLC (57) ABSTRACT

An ammonia gas sensor including a reference electrode (320) is formed on the back surface of a solid electrolyte member (310), and a detection electrode (335) is formed on the front surface of the solid electrolyte member (310). A detection lead (350) is provided on the front surface of the solid electrolyte member (310) such that the detection lead (350) is connected to the detection electrode (335). An insulating layer (340), (380) is provided between the detection lead (350) and the solid electrolyte member (310), or on the detection lead (350).

18 Claims, 8 Drawing Sheets

AMMONIA GAS SENSOR

BACKGROUND OF THE INVENTION

1. Field of the Invention

The present invention relates to an ammonia gas sensor for detecting ammonia gas contained in a gas under measurement.

2. Description of the Related Art

An ammonia gas sensor is disclosed in Patent Document 1. This ammonia gas concentration measurement apparatus includes a solid electrolyte member, a reference electrode provided on one side of the solid electrolyte member, and a detection electrode provided on the opposite side of the solid electrolyte member.

When in use, the reference electrode is exposed to the atmosphere, and the detection electrode is exposed to a gas under measurement. The ammonia gas concentration measurement apparatus generates an electromotive force that is proportional to an electromotive force between the reference electrode and the detection electrode. This in turn depends on the concentration of ammonia gas in the gas under measurement, to thereby detect the concentration of the ammonia gas.

[Patent Document 1] Japanese Patent Application Laid-Open (kokai) No. 2003-83933

3. Problems to be Solved by the Invention

In the ammonia gas concentration measurement apparatus of Patent Document 1, a detection lead is formed to extend from the detection electrode. However, a portion of the detection lead is also exposed to the gas under measurement together with the detection electrode. Since the detection lead is formed of an electrically conductive material such as a noble metal, an electromotive force may be produced between the detection lead and the reference electrode due to ammonia gas in the gas under measurement. As a result, the difference in electromotive force attributable to the detection lead can change the electromotive force thus generated, and may lower accuracy in detecting the concentration of ammonia gas.

SUMMARY OF THE INVENTION

It is therefore an object of the present invention to provide an ammonia gas sensor in which an electromotive force is generated only between a reference electrode and a detection electrode but not between a detection lead and the reference electrode, and which gas sensor can accurately detect the concentration of ammonia (gas) in a gas under measurement.

The above objects have been achieved, in accordance with a first aspect (1) of the invention, by providing an ammonia gas sensor comprising a solid electrolyte member which extends in an axial direction and contains zirconia as a predominant component; a detection portion provided on a front surface of the solid electrolyte member; a reference electrode provided on a back surface of the solid electrolyte member; a detection lead provided directly, or via another member, on the front surface of the solid electrolyte member so as to establish electrical connection between the detection portion and an external circuit; and an insulating portion provided at least on a surface of the detection lead or between the detection lead and the solid electrolyte member.

In the case where the insulating portion is formed on the surface of the detection lead, the detection lead is isolated from the gas under measurement by means of the insulating portion. Therefore, an electromotive force is not generated between the detection lead and the reference electrode at a position where the detection lead is shielded from the gas under measurement.

In the case where the insulating portion is provided between the detection lead and the solid electrolyte member, the detection lead is insulated from the solid electrolyte member by means of the insulating portion. Therefore, even when the detection lead is exposed to the gas under measurement, an electromotive force is not generated between the detection lead and the reference electrode.

Accordingly, in either case, the above-described ammonia gas sensor can prevent generation of an electromotive force between the detection lead and the reference electrode. As a result, the sensor can accurately detect the concentration of ammonia in the gas under measurement.

Preferably, the insulating portion is provided on the surface of the detection lead and between the detection lead and the solid electrolyte member. In the case where the insulating portion is provided on the surface of the detection lead and between the detection lead and the solid electrolyte member, the detection lead is isolated from the gas under measurement by means of one insulating portion, and is insulated from the solid electrolyte member by means of the other insulating portion. Therefore, the generation of an electromotive force between the detection lead and the reference electrode can be reliably prevented.

The insulating portion may be formed only on the surface of the detection lead or only between the detection lead and the solid electrolyte member. Further, the insulating portion may be formed beyond the surface of the detection lead or the interface between the detection lead and the solid electrolyte member.

In a preferred embodiment (2) as applied to (1) above, the detection portion includes a detection electrode formed of a noble metal and a selective reaction layer formed of a metal oxide having ammonia gas selectivity.

By virtue of this configuration, the selective reaction layer exhibits good selectivity for ammonia gas. More particularly, the selective reaction layer removes interfering gases in the gas under measurement, other than ammonia gas, and allows ammonia gas to reach the solid electrolyte member. Thus, the detection electrode can exhibit good current collecting action based on exposure to ammonia gas. As a result, the concentration of ammonia gas between the detection electrode and the reference electrode can be detected accurately.

In another preferred embodiment (3), as applied to (2) above, the detection electrode is provided directly, or via another member, on the solid electrolyte member; and the selective reaction layer is provided directly, or via another member, on the detection electrode. By virtue of this configuration, the gas under measurement is first exposed to the selective reaction layer, so that after interfering gases in the gas under measurement other than ammonia gas are sufficiently burned at the selective reaction layer, the ammonia gas reaches the solid electrolyte member. As a result, the concentration of ammonia can be detected more accurately.

In yet another preferred embodiment (4), as applied to (2) and (3) above, the insulating portion is formed on the surface of the detection lead, and includes a first insulating portion which extends in the axial direction onto the surface of the detection electrode. By virtue of this configuration, even when the ammonia gas sensor is exposed to a gas under measurement, the detection lead is isolated from the gas under measurement by means of the insulating portion. In addition, since the first insulating portion is provided on the surface of the detection electrode near the detection lead, the detection lead is shielded from exposure to the gas under measurement through the detection electrode. Therefore, the detection lead is almost completely isolated from the gas under measurement. Accordingly, an electromotive force is hardly generated between the detection lead and the reference electrode, and, as a result, the concentration of ammonia in the gas under measurement can be detected more accurately.

In yet another preferred embodiment (5), as applied to (4) above, a length of the first insulating portion as measured in the axial direction is greater than a thickness of the detection electrode. By virtue of this configuration, a phenomenon in which the gas under measurement reaches the detection lead while flowing around the first insulating portion whose length is greater than the thickness of the detection electrode hardly occurs, and the detection lead can be isolated almost completely from the gas under measurement.

In yet another preferred embodiment (6), as applied to (2) to (5) above, the insulating portion is provided between the detection lead and the solid electrolyte member, and includes a second insulating portion extending in the axial direction between the detection electrode and the solid electrolyte member. By virtue of this configuration, the detection lead is insulated from the solid electrolyte member by means of the insulating portion. Therefore, even when the detection lead is exposed to the gas under measurement, an electromotive force is not generated between the detection lead and the reference electrode. In addition, the second insulating portion is provided between the solid electrolyte member and a portion of the detection electrode, the portion being located near the detection lead. This configuration suppresses generation of an electromotive force between the detection lead and the reference electrode located near the detection lead. As a result, the concentration of ammonia in the gas under measurement can be detected more accurately.

In yet another preferred embodiment (7) as applied to (6) above, a length of the second insulating portion as measured in the axial direction is greater than a thickness of the detection electrode. This configuration can suppress generation of an electromotive force between the detection lead and the reference electrode layer located near the detection lead via a path flowing around the second insulating portion whose length is greater than the thickness of the detection electrode.

In yet another preferred embodiment (8), as applied to (7) above, the length of the first insulating portion as measured in the axial direction is greater than that of the second insulating portion. The gas under measurement is prevented from reaching the detection lead by making the first insulating portion longer than the second insulating portion. This configuration more reliably prevents the generation of an electromotive force between the detection lead and the reference electrode. As a result, the concentration of ammonia in the gas under measurement can be detected accurately.

In yet another preferred embodiment (9), as applied to (1) to (8) above, the solid electrolyte member assumes the form of a tube having a bottom at a front end portion thereof; the reference electrode is formed on an inner surface of the solid electrolyte member; the detection portion is provided on an outer surface of the front end of the solid electrolyte member; and the detection lead assumes the form of a strip and axially extends rearward from the detection portion. Even in an ammonia gas sensor which comprises a tubular solid electrolyte member having a direction portion provided on an outer surface of a front end portion, and a strip-shaped detection lead extending rearward in the axial direction from the detection portion, by providing an insulating layer at least on the surface of the detection lead or between the detection lead and the solid electrolyte member, it becomes possible to prevent the generation of an electromotive force between the detection lead and the reference electrode, and allows for accurate detection of the concentration of ammonia gas in the gas under measurement.

In yet another preferred embodiment (10), as applied to (9) above, the reference electrode and the detection lead face one another via the solid electrolyte member. In this structure, an electromotive force is likely to generate between the detection lead and the reference electrode. However, by providing an insulating layer at least on the surface of the detection lead or between the detection lead and the solid electrolyte member, it becomes possible to prevent the generation of an electromotive force between the detection lead and the reference electrode, and to accurately detect the concentration of ammonia in the gas under measurement.

In yet another preferred embodiment (11), as applied to (9) and (10) above, the ammonia gas sensor comprises a heater disposed in the tubular solid electrolyte member so as to contact the reference electrode, and the position of contact between the heater and the reference electrode is located frontward of the insulating portion. The ammonia gas sensor may be configured such that the heater is brought into contact with the solid electrolyte member (specifically, the heater is brought into contact with the reference electrode formed on the inner surface of the solid electrolyte member) in order to quickly activate the solid electrolyte member. In such case, by locating the position of contact between the heater and the reference electrode frontward of the insulating portion, a portion of the solid electrolyte member where the reference electrode and the detection electrode for detecting the concentration of ammonia gas are disposed can be activated quickly.

In yet another preferred embodiment (12), as applied to (11) above, the heater includes a heating resistor disposed in a front end portion thereof and a heater lead extending rearward from the heating resistor, and the heating resistor is located frontward of the insulating layer. This configuration enables concentrated heating of the portion of the solid electrolyte member where the reference electrode and the detection electrode for detecting the concentration of ammonia gas are disposed.

In yet another preferred embodiment (13), as applied to (1) to (9) above, the solid electrolyte member assumes the form of a plate extending in the axial direction; the detection portion is provided on a front surface of a front end portion of the solid electrolyte member; and the detection lead assumes the form of a strip extending rearward in the axial direction from the detection portion. Even in an ammonia gas sensor which comprises a plate-shaped solid electrolyte member having a detection portion on the front surface of the front end portion, and a strip-shaped detection lead extending rearward from the detection portion, by providing a strip-shaped insulating layer at least on the surface of the detection lead or between the detection lead and the other surface of the solid electrolyte member, it becomes possible to prevent the generation of an electromotive force between the detection lead and the reference electrode, and to accurately detect the concentration of ammonia in the gas under measurement.

In yet another preferred embodiment (14), as applied to (2) to (13) above, the selective reaction layer covers the detection electrode such that the detection electrode is not exposed. Since the detection electrode is covered by the selective reaction layer such that the detection electrode is not exposed, the gas under measurement passes through the selective reaction layer, without fail, before reaching the solid electrolyte member. Consequently, the ammonia gas reaches the solid electrolyte member after interfering gases in the gas under measurement other than ammonia gas have burned almost completely at the selective reaction layer. As a result, the concentration of ammonia gas can be detected accurately.

In yet another preferred embodiment (15), as applied to (2) to (14) above, the detection electrode and the detection lead each independently contains one of gold and platinum as a predominant component. When gold, platinum, their alloys, or the like is used for the detection electrode and the detection lead, the ammonia gas sensor can effectively exhibit a current collecting action upon exposure to ammonia gas, and can transmit an electromotive force to an external circuit.

In yet another preferred embodiment (16), as applied to (15) above, the detection electrode includes zirconia, and the detection lead includes alumina. By virtue of this configuration, the detection electrode has improved adhesion to the solid electrolyte member, and the detection lead has improved adhesion to the insulating portion.

In yet another referred embodiment (17), as applied to (1) above, the insulating portion contains, as a predominant component, one of alumina, silica, silica alumina, mullite, silicate glass, borate glass, borosilicate glass and phosphate glass. This configuration can prevent the gas under measurement from reaching the detection lead, and insulate the detection lead from the solid electrolyte member.

In yet another preferred embodiment (18), as applied to (2) to (17) above, the metal oxide is vanadium oxide, bismuth oxide, or a composite oxide of vanadium oxide and bismuth oxide such that selectivity for ammonia gas is further ensured.

In yet another preferred embodiment (19) as applied to (2) to (18) above, the selective reaction layer includes palladium in place of at least part of the metal oxide. Even when palladium is used in place of the metal oxide, the gas selectivity for ammonia gas can be secured satisfactorily.

DESCRIPTION OF REFERENCE NUMERALS

Reference numerals used to identify various standard features in the drawings include the following:
310, 940: solid electrolyte member
320, 931: reference electrode
335, 980: detection electrode
340, 380: insulating portion
950, 970: insulating layer
350, 960: detection lead
360, 990: selective reaction layer

DETAILED DESCRIPTION OF THE PREFERRED EMBODIMENTS

Embodiments of an ammonia gas sensor according to the present invention will now be described with reference to the drawings. However, the present invention should not be construed as being limited thereto.

As used herein, "predominant" means an amount greater than 50 wt %.

(Embodiment 1)

Figure 1:
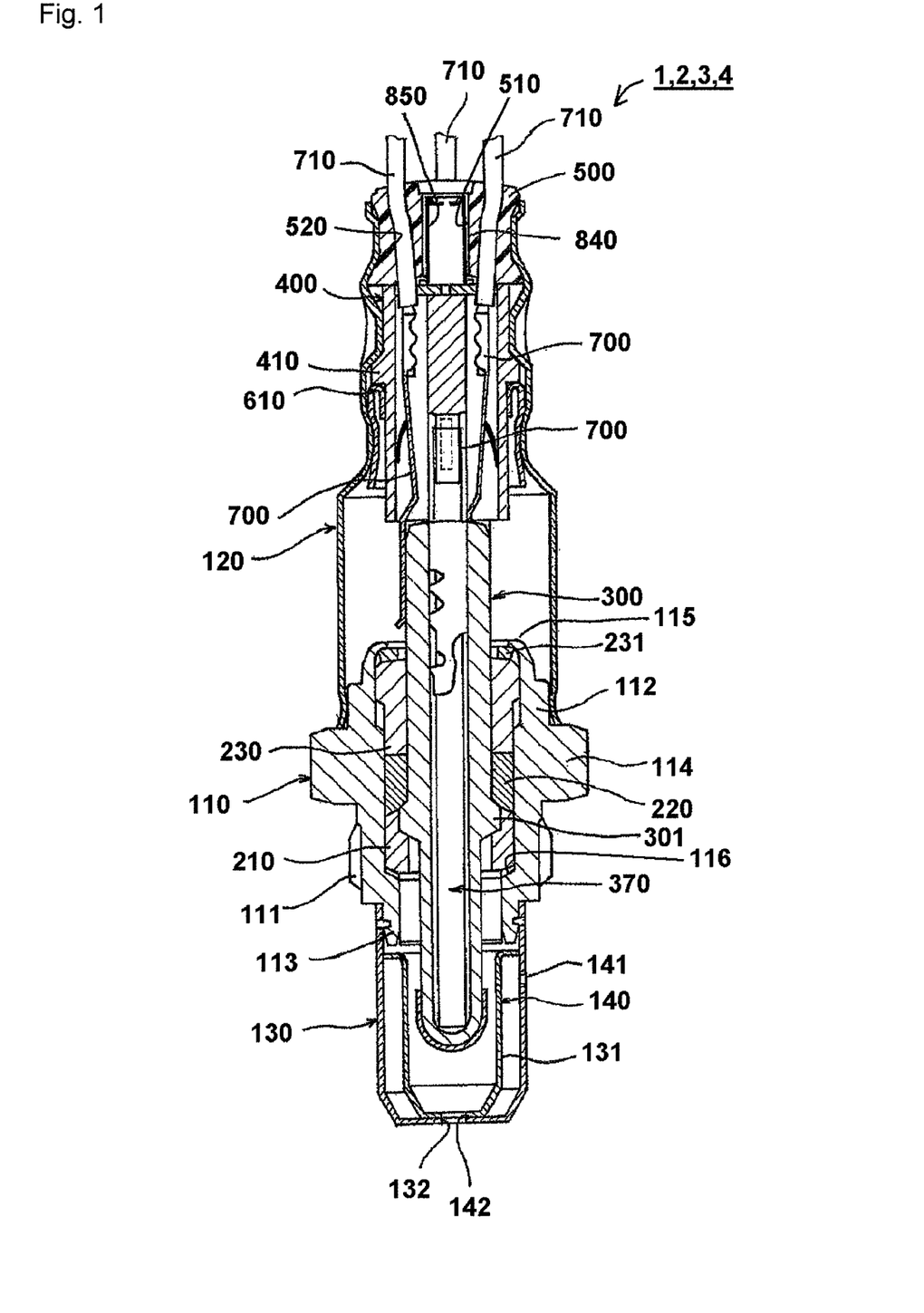
FIG. 1 is a cross sectional view of the ammonia gas sensor 1 of Embodiment 1.

FIG. 1 is a sectional view of an ammonia gas sensor 1 of Embodiment 1. In use, the ammonia gas sensor 1 is attached to, for example, an exhaust pipe (not shown) of an internal combustion engine of an automobile or the like. Notably, in the following description of Embodiment 1, the lower side and upper side of FIG. 1 will be referred to as the front end side and the rear end side, respectively.

The ammonia gas sensor 1 shown in FIG. 1 is configured such that a tubular sensor element 300 closed on its front end side is held in a metallic shell 110. Further, lead wires 710 extend from the ammonia gas sensor 1 so as to extract an output signal of the sensor element 300 and supply electricity to a heater 370 provided adjacent to the sensor element 300. The lead wires 710 are electrically connected to an unillustrated sensor control apparatus or electronic control unit (ECU) of the automobile.

The metallic shell 110 is a tubular member formed of stainless steel such as SUS430, and includes, on its front end side, an external thread portion 111 which is mounted to an exhaust pipe (not shown). Further, a front end engagement portion 113, with which an outer protector 130 to be described below is engaged, is provided on the front end side of the external thread portion 111.

Meanwhile, on the rear end side of the external thread portion 111 of the metallic shell 110, a tool engagement portion 114 is provided, with which an attachment tool is engaged so as to attach the ammonia gas sensor 1 to the exhaust pipe. Further, a crimp portion 115 is provided at the rear end of the metallic shell 110 so as to fixedly crimp the sensor element 300. A rear end engagement portion 112, with which an outer tube 120 described below is engaged, is provided between the tool engagement portion 114 and the crimp portion 115.

A step portion 116 which projects radially inward is provided inside the metallic shell 110. A tubular support member 210 made of alumina is supported on the step portion 116 via a packing made of metal (not shown). The inner circumference of the support member 210 is also shaped to have a step, which supports a flange portion 301 of the sensor element 300 described below, via a packing made of metal (not shown). Further, on the rear end side of the support member 210, a charging material 220 made of talc powder is charged, and a sleeve 230 made of alumina is disposed, so that the charging material 220 is held between the sleeve 230 and the support member 210.

An annular ring 231 is disposed on the rear end side of the sleeve 230. By crimping the crimp portion 115 of the metallic shell 110, the sleeve 230 is pressed against the charging material 220 via the ring 231.

The outer protector 130, which covers a front end portion of the sensor element 300, is attached to the front end engagement portion 113 of the metallic shell 110 by means of welding. An inner protector 140 having the form of a bottomed tube is fixedly provided within the outer projector 130. Introduction openings 131 and 141 are formed in the outer protector 130 and the inner protector 140, respectively, so as to introduce a gas under measurement to the interior of the inner protector 140. Further, discharge openings 132 and 142 are formed in the bottom walls of the outer protector 130 and the inner protector 140, respectively, so as to discharge water droplets and the gas under measurement which have entered the interior of the inner protector 140.

Meanwhile, the tubular outer tube 120 formed of stainless steel such as SUS304 is fixed to the rear end engagement portion 112 of the metallic shell 110 by means of laser welding or the like. The outer tube 120 extends rearward, and surrounds a rear end portion of the sensor element 300 and a separator 400 described below, which is disposed on the rear side of the sensor element 300. Notably, a portion of the outer tube 120 is crimped for engaging and fixing a holding metal piece 610 which holds the separator 400.

The separator 400 holds four connection terminals 700 (FIG. 1 shows three of the connection terminals 700), which are electrically connected to a reference electrode 320 and a detection electrode 335 of the sensor element 300 and a heating resistor of the heater 370. The conductors of the four lead wires 710 are connected to the corresponding connection terminals 700 by means of crimping (FIG. 1 shows three of the lead wires 710). The lead wires 710 extend to the outside of the ammonia gas sensor 1 via a grommet 500, described below. The separator 400 has a flange portion 410, which projects radially outward from the outer circumferential surface of the separator 400. The holding metal piece 610 supports the flange portion 410.

Further, the grommet 500, which has a generally cylindrical columnar shape and is made of a fluoro rubber, is disposed to close the rear end opening of the outer tube 120. A communication hole 510 passes through a radially central portion of the grommet 500 so as to introduce the atmosphere into the interior of the outer tube 120. Moreover, on the radially outer side of the communication hole 510, four lead-wire insertion holes 520 are provided at equal intervals in the circumferential direction. The lead wires 710 are inserted into and passed through the lead-wire insertion holes 520.

A filter member 840 and a retaining metal piece 850 therefor are inserted into the communication hole 510 of the grommet 500. The filter member 840 is a membrane filter which is formed of a fluorocarbon resin such as PTFE (polytetrafluoroethylene) and which has a network structure. The filter member 840 prohibits passage of water droplets or the like therethrough, and allows passage of the atmosphere therethrough. The retaining metal piece 850 is a member formed into a tubular shape, holds the filter 840 between its outer circumference and the inner circumference of the communication hole 510, and is fixed to the grommet 500.

Figure 2:
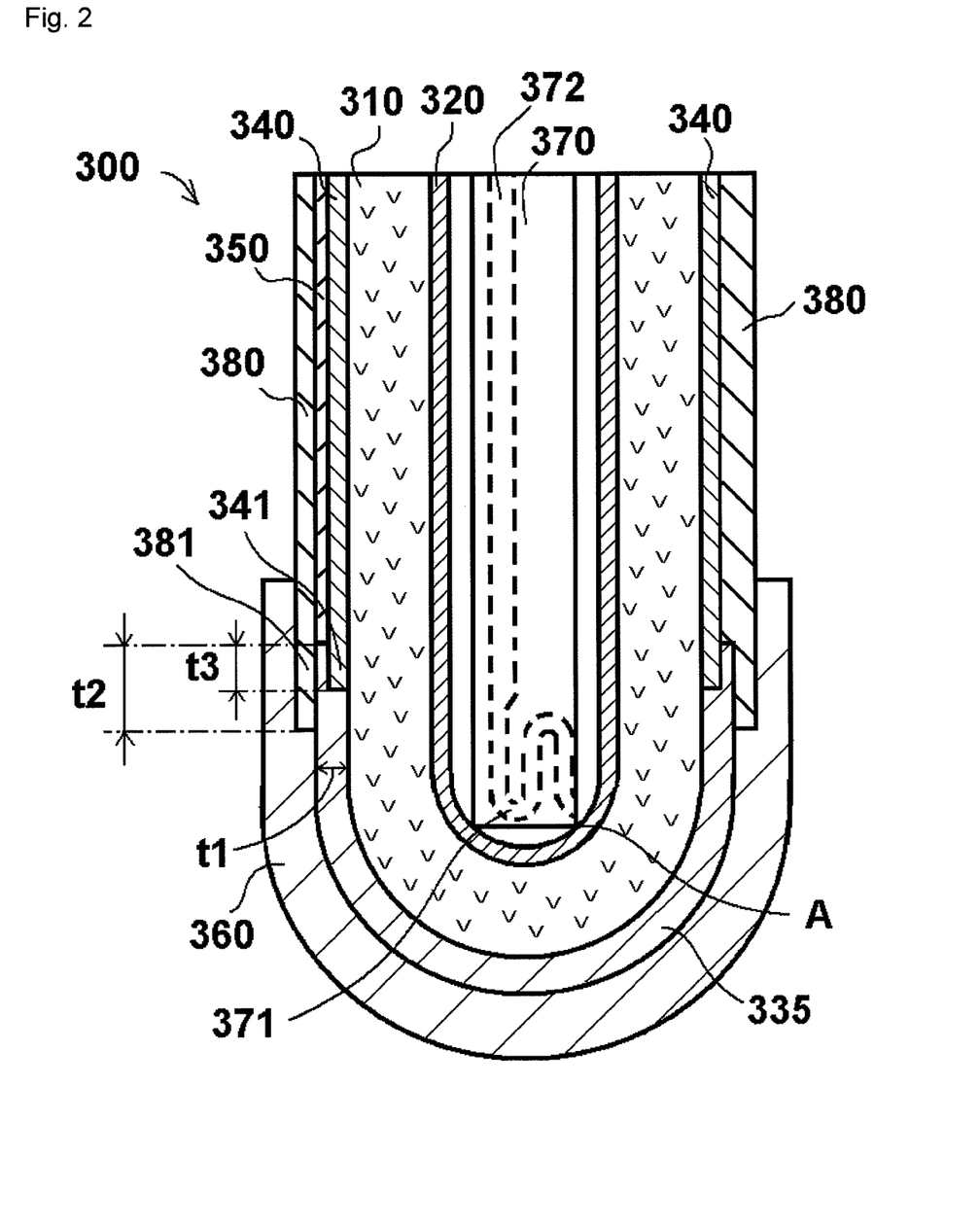
FIG. 2 is an enlarged cross sectional view of a front end portion of the sensor element 300 of FIG. 1.

Next, the sensor element 300 will be described. As shown in FIG. 1, the sensor element 300 includes the flange portion 301, which projects radially outward from a generally central portion of the sensor element 300. As shown in FIG. 2, the sensor element 300 includes a solid electrolyte member 310 which contains zirconia as a predominant component and which has the form of a bottomed tube. Notably, FIG. 2 is an enlarged cross sectional view of a front end portion of the sensor element 300. A bar-shaped heater 370 is inserted into the solid electrolyte member 310 so as to heat and activate the solid electrolyte member 310. This heater 370 includes a heating resistor 371 disposed on the front end side, and a heater lead 372 extending rearward from the heating resistor 371.

The reference electrode 320, whose predominant component is Pt or a Pt alloy, is formed over the entire inner surface of the solid electrolyte member 310. Meanwhile, a detection electrode 335 (thickness: 20 μm) and a selective reaction layer 360 (thickness: 30 μm) are provided on the outer surface of a front end portion of the solid electrolyte member 310. The selective reaction layer 360 is formed of a metal oxide which contains vanadium oxide ($V_2O_5$) and bismuth oxide ($Bi_2O_3$) as predominant components; e.g., bismuth vanadium oxide ($BiVO_4$). Further, a strip-shaped detection lead 350 is formed on the outer surface of the solid electrolyte member 310 such that it extends from the detection electrode 335. The detection electrode 335 and the detection lead 350 are formed of a material which contains gold (Au) as a predominant component.

In the ammonia gas sensor 1 arranged in the above-described manner, the selective reaction layer 360 removes interfering gases from the gas under measurement, and permits ammonia gas to reach the solid electrolyte member 310. Thus, the detection electrode 335 can exhibit a current-collecting action based on ammonia gas. As a result, the concentration of the ammonia gas can be accurately detected.

An insulating layer 340, which contains alumina ($Al_2O_3$) as a predominant component, is provided between the detection lead 350 and the solid electrolyte member 310. Notably, in Embodiment 1, the insulating layer 340 is provided not only between the detection lead 350 and the solid electrolyte member 310, but over the entire outer surface of the solid electrolyte member 310.

Since the insulating layer 340 is provided between the detection lead 350 and the solid electrolyte member 310, the detection lead 350 is insulated from the solid electrolyte member 310 by means of the insulating layer 340. Therefore, even when the detection lead 350 is exposed to the gas under measurement, an electromotive force is not produced between the detection lead 350 and the reference electrode 320.

Further, an insulating layer 380, which contains alumina ($Al_2O_3$) as a predominant component, is provided on the surface of the detection lead 350. Notably, in Embodiment 1, the insulating layer 380 is provided not only on the surface of the detection lead 350, but over the entire surface of the insulating layer 340.

The insulating layer 380 is formed on the surface of the detection lead 350 to isolate the detection lead 350 from the gas under measurement. Therefore, an electromotive force is not produced between the detection lead 350 and the reference electrode 320.

Accordingly, the ammonia gas sensor 1 can prevent the generation of a difference in electromotive force between the detection lead 350 and the reference electrode 320, and, as a result, can accurately detect the concentration of ammonia in the gas under measurement.

The insulating layer 380 includes a first insulating portion 381 which extends in the axial direction onto the surface of the detection electrode 335. The first insulating portion 381 is provided on the surface of the detection electrode 335 near the detection lead 350. This configuration suppresses exposure of the detection lead 350 to the gas under measurement through the detection electrode 335. Therefore, the detection lead 350 is substantially isolated from the gas under measurement. Therefore, only a small difference in electromotive force is produced between the detection lead 350 and the reference electrode 320, and, as a result, the concentration of ammonia gas in the gas under measurement can be detected more accurately.

The axial length t2 of the first insulating portion 381 is 100 μm, which is greater than the thickness t1 of the detection electrode 335. Therefore, a case in which the gas under measurement flows around the first insulating portion 381 and reaches the detection lead 350 hardly occurs, and the detection lead 350 can be almost completely isolated from the gas under measurement.

Meanwhile, the insulating portion 340 includes a second insulating portion 341 which axially extends between the detection electrode 335 and the solid electrolyte member 310. The second insulating portion 341 is provided between the solid electrolyte member 310 and a portion of the detection electrode 335, the portion being located near the detection lead 350. This configuration suppresses the generation of an electromotive force between the detection lead 350 and the reference electrode 320 located near the detection lead 350. As a result, the concentration of ammonia in the gas under measurement can be detected more accurately.

The axial length t3 of the second insulating portion 341 is 50 μm, which is greater than the thickness t2 of the detection electrode 335. Therefore, it becomes possible to prevent the generation of an electromotive force between the detection lead 350 and the reference electrode 320 located near the detection lead 350 via a path around the second insulating portion 341. As a result, the concentration of ammonia in the gas under measurement can be accurately detected.

In addition, the axial length t2 of the first insulating portion 381 is greater than the axial length t3 of the second insulating portion 341. This prevents the gas under measurement from reaching the detection lead 350, to thereby more reliably prevent the generation of an electromotive force between the detection lead 350 and the reference electrode 320. As a result, the concentration of ammonia in the gas under measurement can be detected accurately.

In the configuration of Embodiment 1, in which the reference electrode 320 and the detection lead 350 face one another via the solid electrolyte member 310, an electromotive force is likely to develop, in particular, between the detection lead 350 and the reference electrode 320. However, by providing the insulating layers 340 and 380, the generation of an electromotive force between the detection lead 350 and the reference electrode 320 can be prevented, and the concentration of ammonia in the gas under measurement can be detected accurately.

Moreover, the position A of contact between the heater 370 and the reference electrode 320 is located frontward of the insulating portions 340 and 380. Therefore, the front end portion of the solid electrolyte member 310 where the detection electrode 335 and the reference electrode 320 are provided can be activated quickly.

Also, the heating resistor 371 is located frontward of the insulating layers 340 and 380. Therefore, the front end portion of the solid electrolyte member 310 where the detection electrode 335 and the reference electrode 320 are provided can be heated in a concentrated manner.

Moreover, the selective reaction layer 360 covers the detection electrode 335 such that the detection electrode 335 is not exposed. This configuration ensures that the gas under measurement passes through the selective reaction layer 360, without fail, before reaching the solid electrolyte member 310. In this manner, the ammonia gas reaches the solid electrolyte member 310 only after interfering gases in the gas under measurement other than ammonia gas have burned almost completely at the selective reaction layer 360.

Next, a method of manufacturing the ammonia gas sensor 1 of Embodiment 1 will be described.

1. Step of Forming the Solid Electrolyte Member 310

A powder of partially stabilized zirconia is prepared, and is charged into a bottomed-tubular rubber mold (not shown). The partially stabilized zirconia is obtained by adding 4.5 mol % of yttrium oxide ($Y_2O_3$) (stabilizer) to zirconia ($ZrO_2$). The powder of partially stabilized zirconia is press-molded into a bottomed-tubular shape within the rubber mold, followed by firing at 1490° C. Thus, the solid electrolyte member 310 having a bottomed-tubular shape is fabricated.

2. Step of Forming the Reference Electrode 320

Next, platinum (Pt) is applied to the inner surface of the solid electrolyte member 310 by means of electroless plating, and then fired. Thus, the reference electrode 320 is formed on the inner surface of the solid electrolyte member 310.

3. Step of Forming the Insulating Layer 340

Subsequently, alumina ($Al_2O_3$), an organic solvent and a dispersant are mixed to provide a dispersion mixture. Then, a binder and a viscosity modifier are added to the mixture in respective predetermined amounts, and the mixture is subjected to wet blending. Thus, a paste for an insulating layer, which is to become the insulating layer 340 after firing, is prepared.

The paste for the insulating layer is applied to the outer surface of the solid electrolyte member 310, and is dried, followed by firing at 1400° C. for one hour. Thus, the insulating layer 340 is formed over the entire outer surface of the solid electrolyte member 310.

4. Step of Forming the Detection Electrode 335 and the Detection Lead 350

Next, gold (Au), zirconia ($ZrO_2$), an organic solvent and a dispersant are mixed to provide a dispersion mixture. Subsequently, a binder and a viscosity modifier are added to the mixture in respective predetermined amounts, and the mixture is subjected to wet blending. Thus, a paste for the detection electrode is prepared.

Further, gold (Au), alumina ($Al_2O_3$), an organic solvent and a dispersant are mixed to provide a dispersion mixture. Subsequently, a binder and a viscosity modifier are added to the mixture in respective predetermined amounts, and the mixture is subjected to wet blending. Thus, a paste for the detection lead is prepared.

The paste for the detection electrode and the paste for detection lead are printed on the outer surface of the solid electrolyte member 310 and the outer surface of the insulating layer 340, which are formed in the above-described manner. After drying, firing is performed at 1000° C. for one hour. Thus, the detection electrode 335 is formed on the outer surface of a front end portion of the solid electrolyte member 310 and the outer surface of a front end portion of the insulating layer 340. Further, the detection lead 350 is formed on the outer surface of the insulating layer 340 such that the detection lead 350 assumes a strip-like shape and extends from the detection electrode 335.

The detection electrode 335 is formed such that it contains zirconia, and the detection lead is formed such that it contains alumina. Therefore, the detection electrode 335 has improved adhesion to the solid electrolyte member 310, and the detection lead 350 has improved adhesion to the insulating portions 340 and 380.

5. Step of Forming the Insulating Layer 380

Next, the above-described paste for an insulating layer is applied to the outer surfaces of the detection electrode 335, the detection lead 350 and the insulating layer 340, and dried, followed by firing at 1000° C. for one hour. Thus, the insulating layer 380 is formed over the entire outer surface of the solid electrolyte member 310.

6. Step of Forming the Selective Reaction Layer 360

Next, a composite oxide composed of vanadium oxide ($V_2O_5$) and bismuth oxide ($Bi_2O_3$), an organic solvent and a dispersant are mixed to provide a dispersion mixture. Subsequently, a binder and a viscosity modifier are added to the mixture in respective predetermined amounts, and the mixture is subjected to wet blending. Thus, a paste for the selective reaction layer is prepared.

The paste for the selective reaction layer is printed on the outer surfaces of the detection electrode 335 and the insulating layer 380, and dried, followed by firing at 750° C. for 10 minutes. Thus, the selective reaction layer 360 made of bismuth vanadium oxide ($BiVO_4$) is formed.

7. Step of Assembling the Ammonia Gas Sensor 1

After the sensor element 300 is fabricated in the above-described manner, the sensor element 300 is held within the metallic shell 110. Subsequently, the separator 400 is held within the outer tube 120 via the holding metal piece 610; and the grommet 500, the terminals 700 and the covered wires 710 are assembled into the outer tube 120. Thus, manufacture of the ammonia gas sensor 1 is completed.

(Embodiment 2)

Figure 3:
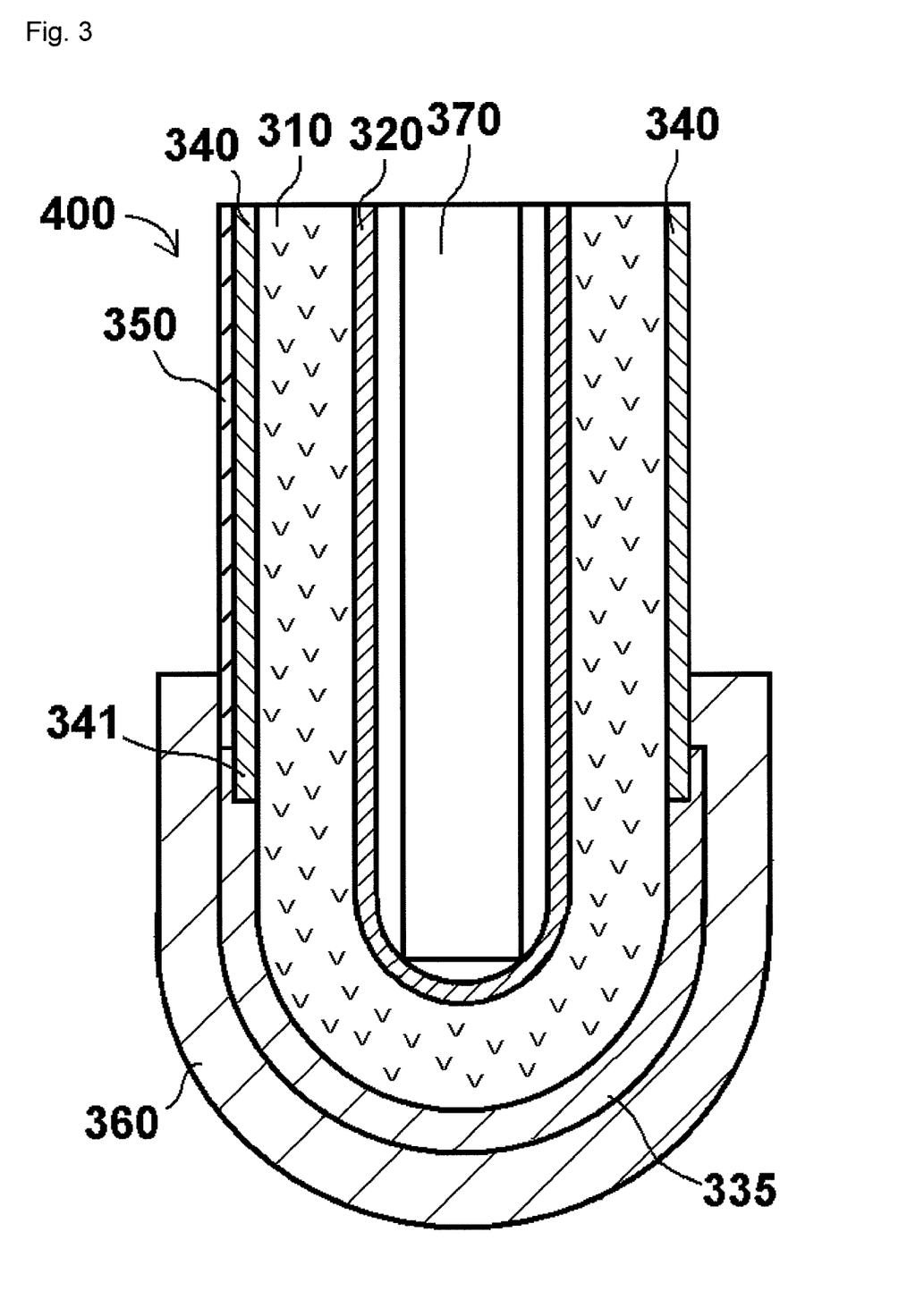
FIG. 3 is an enlarged cross sectional view of a front end portion of the sensor element 400 of the ammonia gas sensor 2 of Embodiment 2.

FIG. 3 is an enlarged cross sectional view of a front end portion of a sensor element 400 attached to an ammonia gas sensor 2 of Embodiment 2. The sensor element 400 of Embodiment 2 differs from the sensor element 300 of Embodiment 1 in that the insulating layer 380 is not provided, and the selective reaction layer 360 is provided directly on the surfaces of the detection electrode 335 and the detection lead 350. For the ammonia gas sensor 2 of Embodiment 2, the same descriptions as for Embodiment 1 will be omitted or simplified, and portions the same as those of Embodiment 1 are denoted by like reference numerals.

In Embodiment 2, the selective reaction layer 360 is provided on the surface of the detection electrode 335 and on the surface of a front end portion of the detection lead 350. The selective reaction layer 360 covers the detection electrode 335 such that the detection electrode 335 is not exposed. Thus, the ammonia gas reaches the detection electrode 335 after interfering gases in the gas under measurement other than ammonia gas have burned almost completely at the selective reaction layer 360. The remaining structure is identical with that of Embodiment 1.

Even in the ammonia gas sensor 2 of Embodiment 2, the insulating portion 340 is provided between the detection lead 350 and the solid electrolyte member 310, so that the detection lead 350 is insulated from the solid electrolyte member 310 by means of the insulating portion 340. Therefore, even when the detection lead 350 is exposed to the gas under measurement, an electromotive force is not generated between the detection lead 350 and the reference electrode 320. As a result, the concentration of ammonia in the gas under measurement can be accurately detected.

(Embodiment 3)

Figure 4:
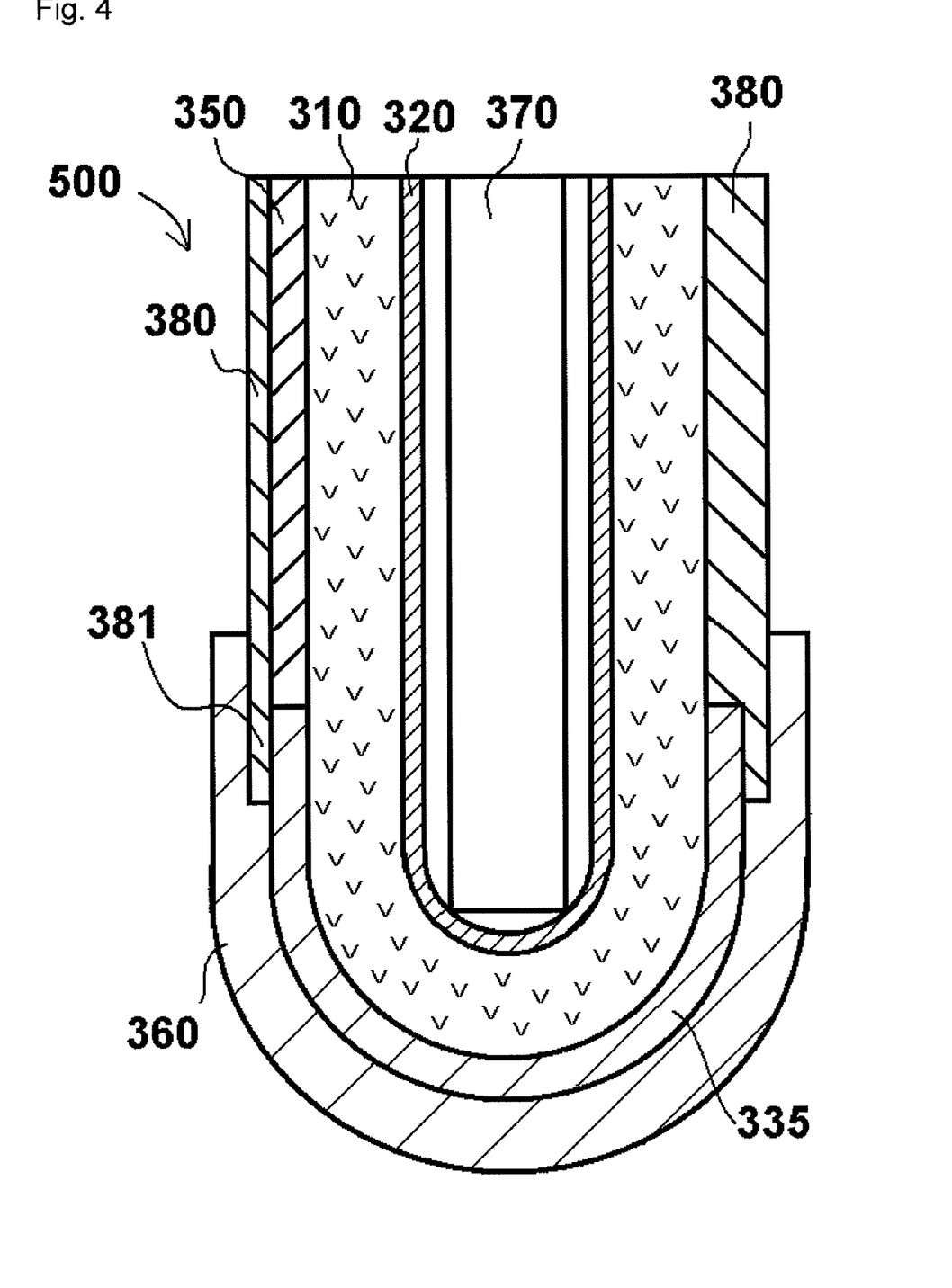
FIG. 4 is an enlarged cross sectional view of a front end portion of the sensor element 500 of the ammonia gas sensor 3 of Embodiment 3.

FIG. 4 is an enlarged cross sectional view of a front end portion of a sensor element 500 attached to an ammonia gas sensor 3 of Embodiment 3. The sensor element 500 of Embodiment 3 differs from the sensor element 300 of Embodiment 1 in that the insulating layer 340 is not provided, and the detection electrode 335 and the detection lead 350 are provided directly on the surface of the solid electrolyte member 310. For the ammonia gas sensor 3 of Embodiment 3, the same descriptions as for Embodiment 1 will be omitted or simplified, and portions the same as those of Embodiment 1 are denoted by like reference numerals.

In Embodiment 3, the detection electrode 335 and the detection lead 350 are provided on the surface of the solid electrolyte member 310; and the insulating layer 380 is provided to cover the detection lead 350. The remaining structure is the same as that of Embodiment 1.

Even in the ammonia gas sensor 3 of Embodiment 3, the insulating portion 380 is formed on the detection lead 350, so that the detection lead 350 is isolated from the gas under measurement by means of the insulating portion 380. Therefore, an electromotive force is not generated between the detection lead 350 and the reference electrode 320. As a result, the concentration of ammonia in the gas under measurement can be accurately detected.

(Embodiment 4)

Figure 5:
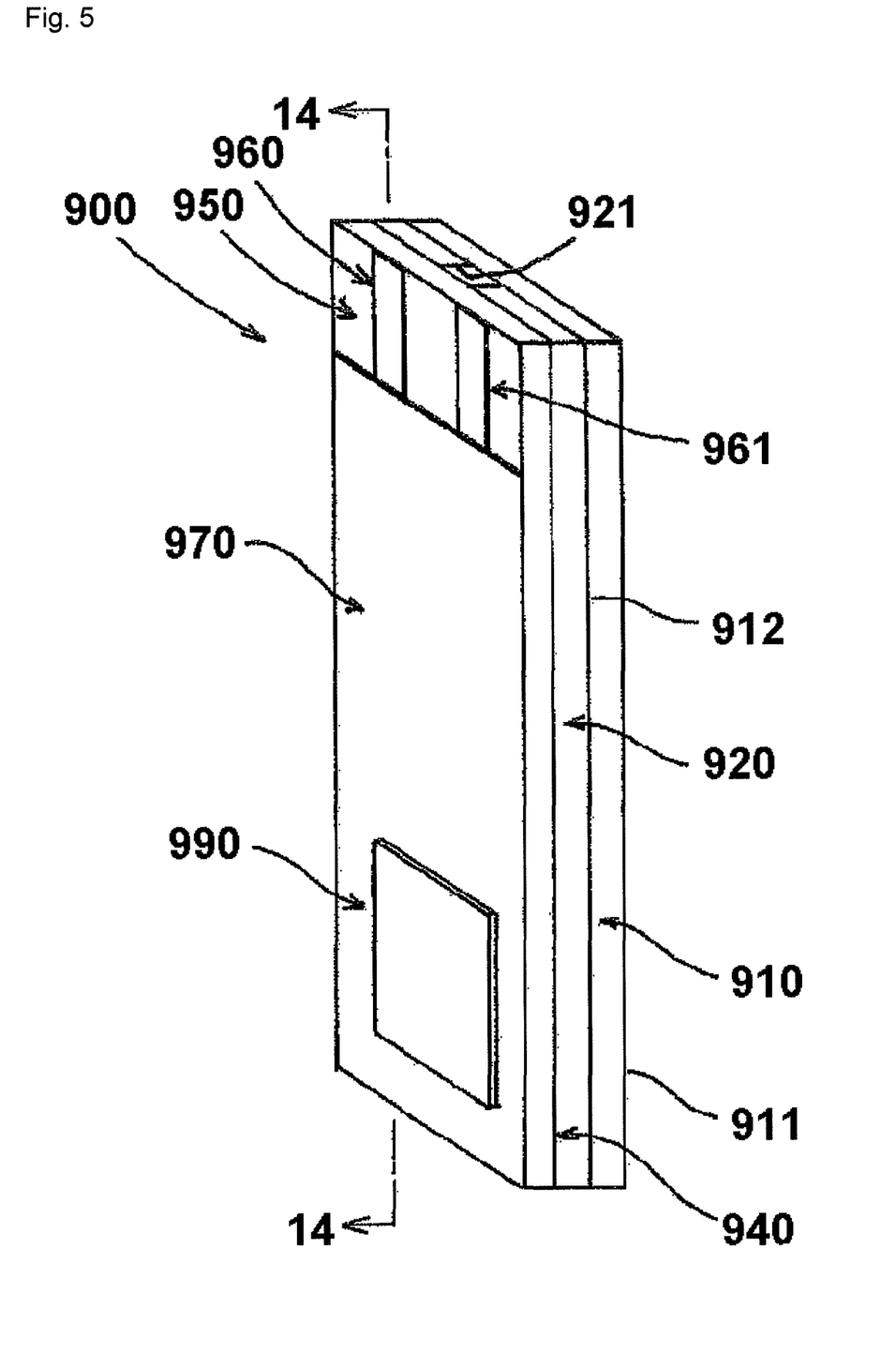
FIG. 5 is a perspective view showing the sensor element 900 of the ammonia gas sensor 4 of Embodiment 4.
Figure 6:
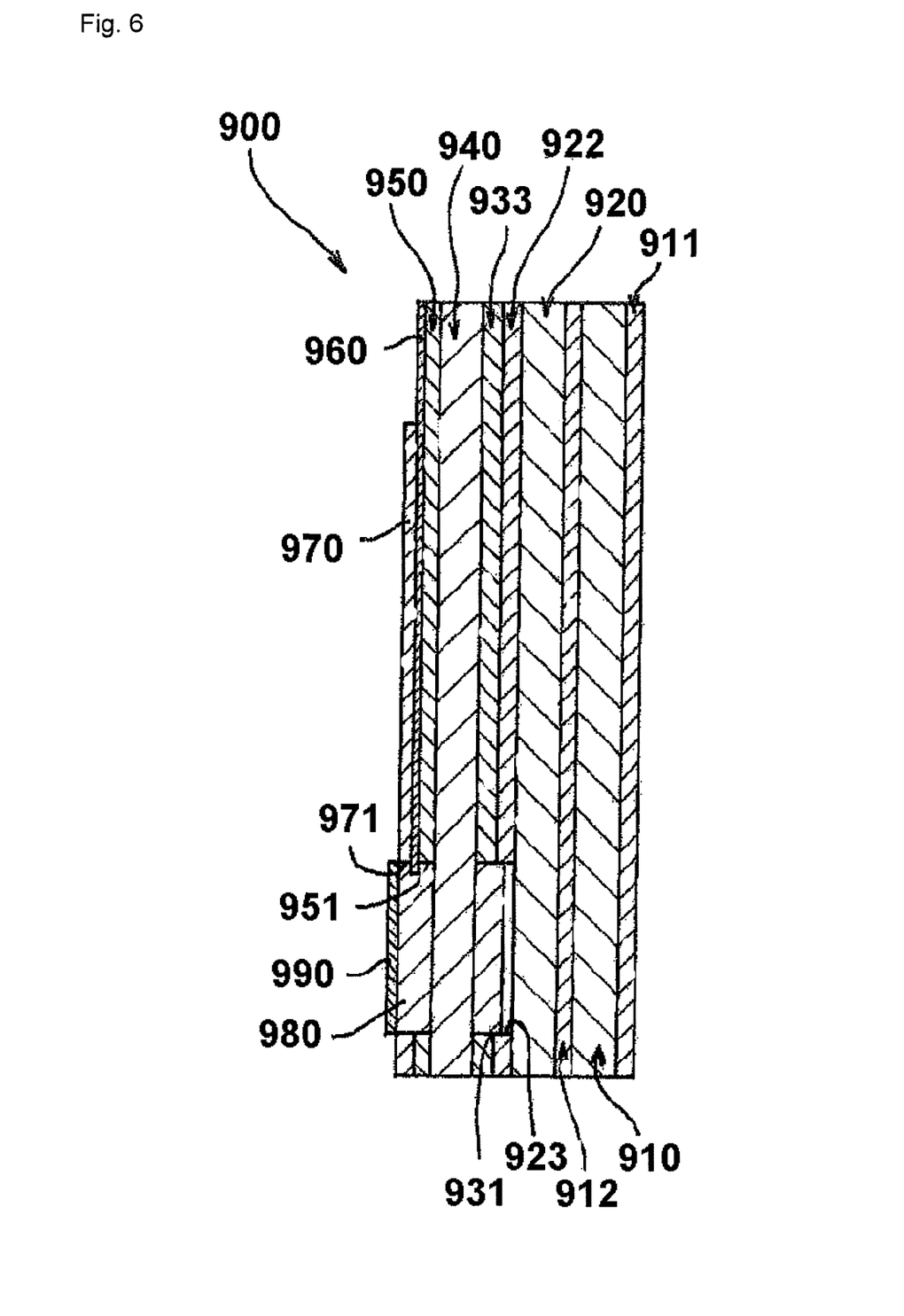
FIG. 6 is a cross sectional view of the sensor element 900 taken along line 14-14 of FIG. 5.
Figure 7:
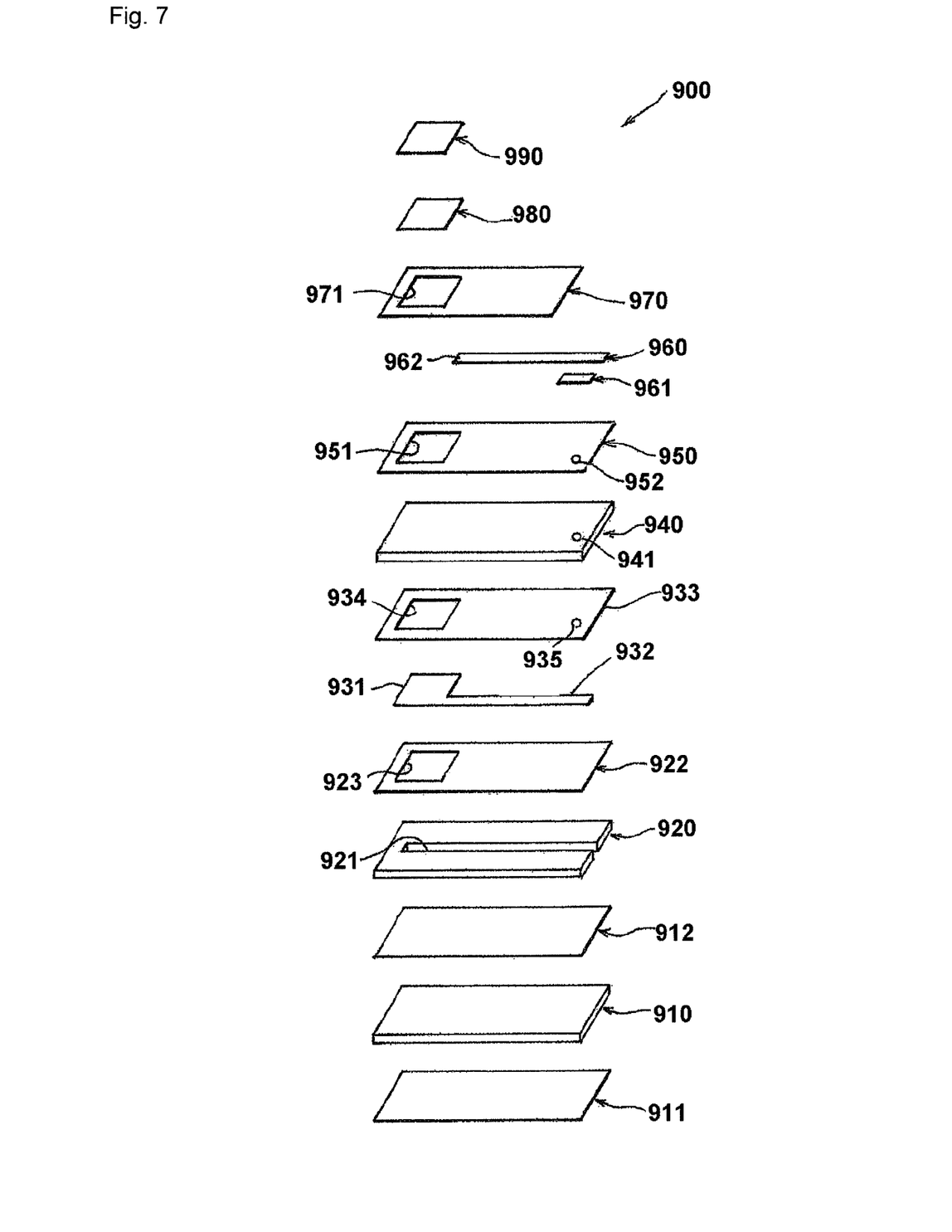
FIG. 7 is an exploded perspective view of the sensor element 900 of FIG. 5.

FIGS. 5 to 7 show a sensor element 900 of an ammonia gas sensor 4 of Embodiment 4. The ammonia gas sensor 4 of Embodiment 4 differs from that of Embodiment 1 in that in place of the gas sensor element 300, a plate-type sensor element 900 is incorporated into the ammonia gas sensor 4. The remaining portions have the same structure as those of Embodiment 1. Notably, for the ammonia gas sensor 4 of Embodiment 4, the same descriptions as for Embodiment 1 will be omitted or simplified, and portions the same as those of Embodiment 1 are denoted by like reference numerals.

The plate-type sensor element 900 is coaxially held within the metallic shell 110. The sensor element 900 includes a solid electrolyte member 940 formed of the same material as the solid electrolyte member 310 of Embodiment 1.

A reference electrode 931 and a reference lead 932, which are formed of the same material as the reference electrode 320 of Embodiment 1, are provided on the back surface of the solid electrolyte member 940 via an insulating film 933. The reference electrode 931 is disposed at a position corresponding to an opening portion 934 formed in a front end portion of the insulating film 933, and is in close contact with a front end portion of the solid electrolyte member 940. Meanwhile, the reference lead 932 is formed to extend from a front end portion toward a rear end portion of the back surface of the insulating film 933. The reference lead 932 is electrically connected to an electrode pad 961 via a through-hole 935 of the insulating film 933, a through-hole 941 of the solid electrolyte member 940, and a through-hole 952 of an insulating film 950 described below.

Further, an insulating film 922 including opening portion 923, a sealing layer 920, an insulating film 912, a support layer 910, and an insulating film 911 are stacked in this sequence on the back surface of the insulating film 933 such that the reference electrode 931 and the reference lead 932 are sandwiched therebetween. Of these films and layers, the sealing layer 920 has a communication groove portion 921 extending from a front end side toward the rear end side thereof. This communication groove portion 921 establishes communication between the atmosphere and the reference electrode 931.

Meanwhile, a detection lead 960 and an electrode pad 961, which are formed of a material which contains platinum (Pt) (predominant component) and alumina, are formed on the front surface of the solid electrolyte member 940 via an insulating film 950. The detection lead 960 and the electrode pad 961 extend along the surface of the insulating film 950 from the front end side toward the rear end side thereof. A front end portion 962 of the detection lead 960 is extended into an opening portion 951 of the insulating film 950 for connection with a detection electrode 980 described below.

Moreover, an insulating film 970 is stacked on the surface of the insulating film 950 such that the detection lead 960 is sandwiched therebetween. This insulating film 970 has an opening portion 971 at its front end. The opening portion 971 is formed such that it coincides with the opening portion 951 of the insulating film 950.

Furthermore, the detection electrode 980, which is formed of the same material as the detection electrode 335 described in Embodiment 1, is provided in the opening portion 971 of the insulating film 970 and the opening portion 951 of the insulating film 950. The detection electrode 980 is in close contact with the front surface of the solid electrolyte member 940. Further, a selective reaction layer 990, which is formed of the same material as the selective reaction layer 360 described in Embodiment 1, is provided on the surface of the detection electrode 980.

Since the insulating layer 950 is provided between the detection lead 960 and the solid electrolyte member 940 as described above, the detection lead 960 is insulated from the solid electrolyte member 940 by means of the insulating portion 950. Therefore, even when the detection lead 960 is exposed to the gas under measurement, an electromotive force is not generated between the detection lead 960 and the reference lead 932.

In addition, since the insulating layer 970 is formed on the surface of the detection lead 960, the detection lead 960 is isolated from the gas under measurement by means of the insulating layer 970. Therefore, an electromotive force is not generated between the detection lead 960 and the reference lead 932.

Accordingly, the ammonia gas sensor 4 can prevent the generation of an electromotive force between the detection lead 960 and the reference lead 932, and, as a result, can accurately detect the concentration of ammonia in the gas under measurement.

Next, a method of manufacturing the ammonia gas sensor 4 will be described. The paste for the insulating layer of Embodiment 1 is printed on the back surface of a previously prepared green sheet, which is to become the solid electrolyte member 940, such that the paste is applied in a region corresponding to the insulating film 933, and then dried. The green sheet is formed of partially stabilized zirconia obtained by adding 5.4 mol % of yttrium oxide ($Y_2O_3$) (stabilizer) to zirconia ($ZrO_2$).

Next, platinum (Pt) (predominant component) and partially stabilized zirconia of 14% (weight ratio with respect to the platinum) are mixed to provide a dispersion, together with an organic solvent and a dispersant. Next, a binder and a viscosity modifier are added to the mixture in respective predetermined amounts, and the mixture is subjected to wet blending. Thus, a paste for an electrode is prepared. Notably, a few wt % of gold (Au) may be added to the platinum in order to suppress the catalytic activity of the platinum.

Subsequently, the paste for an electrode is screen-printed on the above-described paste film for the insulating film 933 such that the paste for the electrode is applied to regions corresponding to the reference electrode portion 931 and the reference lead 932, and then dried. After that, the paste for insulating layer of Embodiment 1 is printed on the paste film for the insulating film 933 via the paste for electrode layer such that the paste for the insulating layer is applied to a region corresponding to the insulating film 922, and then dried.

Meanwhile, the paste for the insulating layer of Embodiment 1 is printed on the front surface of the green sheet such that the paste is applied to a region corresponding to the insulating film 950, and then dried. Next, the paste for the electrode layer is printed on the paste for the insulating layer 950 such that the paste for electrode layer is applied to regions corresponding to the detection lead 960 and electrode pad 961, and then dried.

Subsequently, the paste for the insulating layer of Embodiment 1 is printed on the paste for the insulating film 950 via the paste for an electrode such that the paste for insulating layer is applied to a region corresponding to the insulating film 970, and then dried. Next, predetermined pastes which are to become the support layer 910 and the sealing layer 920 are printed, dried, and compression-bonded, followed by debindering at 400° C. and firing at 1470° C. Notably, a heater and a temperature-measurement resistor (not shown) are bonded to the insulating film 911 of the above-described sensor element structure. However, the heater and the temperature-measurement resistor may be incorporated into the sensor element structure.

After that, the paste for the detection electrode described in Embodiment 1 is screen-printed in an opening portion of the paste for the insulating film 970 (corresponding to the opening portion 971 of the insulating film 970) such that the paste for the detection electrode is applied to a region corresponding to the detection electrode 980 and comes into close contact with the front surface of the green sheet. The paste for detection electrode is then dried, and fired at 1000° C. for one hour.

Finally, the paste for the selective reaction layer described in Embodiment 1 is screen-printed on the detection electrode 980, and then fired at 750° C. for 10 minutes. Thus, the fabrication of the sensor element 900 is completed.

Test Example

The characteristics of the ammonia gas sensors 1 to 3 of Embodiment 1 to Embodiment 3 were evaluated. For this evaluation, the ammonia gas sensor 1 of Embodiment 1 is referred to as "Example 1," the ammonia gas sensor 2 of Embodiment 2 is referred to as "Example 2," and the ammonia gas sensor 3 of Embodiment 3 is referred to as "Example 3." Further, an ammonia gas sensor serving as a Comparative Example was prepared for comparison. The ammonia gas sensor of the Comparative Example was configured such that the insulating layers 340 and 380 were not provided, and the detection lead 350 was disposed directly on the outer surface of the solid electrolyte member 310.

For carrying out the above-described evaluation, a model gas generation apparatus was used as an evaluation apparatus. The model gas generation apparatus generates a gas for evaluation as described below.

First, a base gas was prepared containing 10% oxygen ($O_2$), 5% carbon dioxide ($CO_2$), 5% water ($H_2O$) and balance nitrogen ($N_2$), by volume. Subsequently, 10 ppm or 100 ppm of ammonia ($NH_3$) and 100 ppm of propylene ($C_3H_6$) were selectively added to the base gas to obtain the gas for evaluation. The temperature of the gas for evaluation was set to 280° C.

Examples 1 to 3 and the Comparative Example were placed in the gas for evaluation within the model gas generation apparatus. Then, for each of Examples 1 to 3 and Comparative Example, a potential difference produced between the reference electrode 320 and the detection electrode 335 was measured. Notably, the temperatures of Examples 1 to 3 and Comparative Example were controlled and maintained at 650° C. by action of the heater 370.

Figure 8:
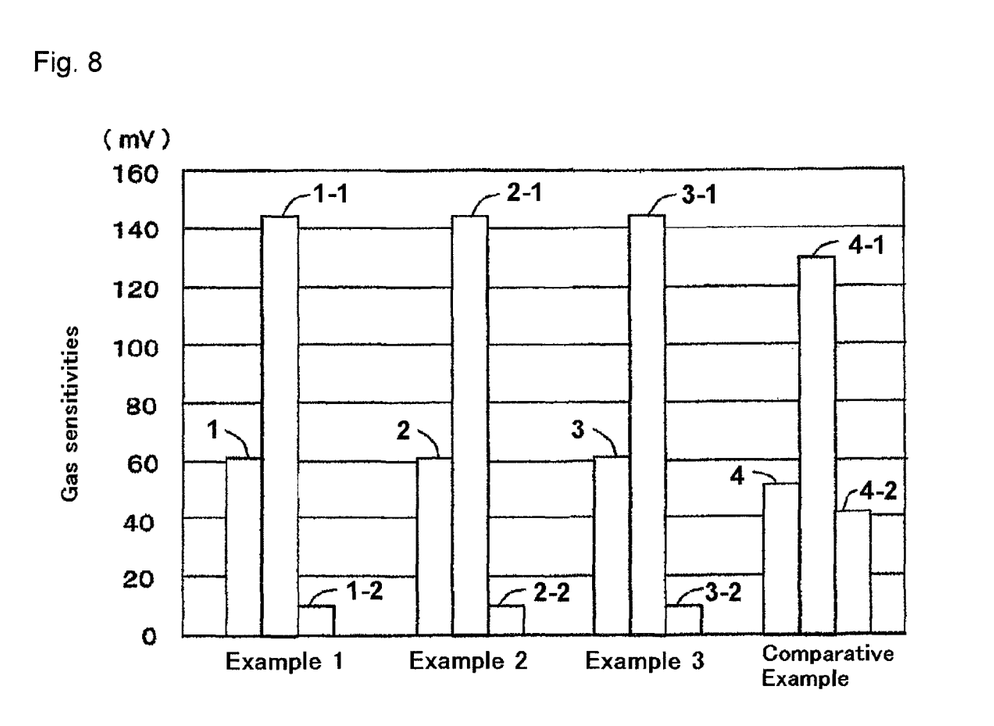
FIG. 8 shows the relationship between the gas sensitivities of Embodiments 1 to 3 and the Comparative Example and the concentrations of ammonia and propylene gases.

For each of Examples 1 to 3 and Comparative Example, the relationship between gas sensitivity (mV) and the ammonia or propylene of the gas for evaluation was measured. Notably, the gas sensitivity is obtained by subtracting an electromotive force generated in the presence of the base gas from an electromotive force generated when ammonia or propylene is added to the base gas. FIG. 8 shows the results.

In FIG. 8, bars 1 to 1-2 show the gas sensitivities of Example 1; bars 2 to 2-2 show the gas sensitivities of Example 2; bars 3 to 3-2 show the gas sensitivities of Example 3; and bars 4 to 4-2 show the gas sensitivities of the Comparative Example. Further, bars 1 to 4 show the respective gas sensitivities of Examples 1 to 3 and the Comparative Example for the case where the gas for evaluation was prepared by adding 10 ppm of ammonia to the base gas. Bars 1-1 to 4-1 show the respective gas sensitivities of Examples 1 to 3 and the Comparative Example for the case where the gas for evaluation was prepared by adding 100 ppm of ammonia to the base gas. Bars 1-2 to 4-2 show the respective gas sensitivities of Examples 1 to 3 and the Comparative Example for the case where the gas for evaluation was prepared by adding 100 ppm of propylene to the base gas.

The ammonia sensors of Examples 1 to 3 each exhibited a higher gas sensitivity, as compared with the ammonia sensor of the Comparative Example, for the case where 10 ppm of ammonia was added (bars 1 to 3) and the case where 100 ppm of ammonia was added (bars 1-1 to 3-1). The ammonia sensors of Examples 1 to 3 each exhibited a lower gas sensitivity, as compared with the ammonia sensor of the Comparative Example, for the case where propylene was added (bars 1-2 to 3-2).

The present invention is not limited to the above-described embodiments, and may be modified in practice. For example:

(1) Instead of gold, the detection electrode material used for forming the detection electrodes 335 and 980 may contain platinum (Pt), or platinum and gold as a predominant component. The predominant component is not limited to gold and platinum, and may be another noble metal.

(2) The material of the detection leads 350 and 960 is not limited to the detection electrode material containing gold (Au) as a predominant component. The material of the detection leads 350 and 960 may contain platinum (Pt), or platinum and gold as a predominant component.

(3) The material of the insulating layers 340, 380 and the insulating films 950, 970 is not limited to alumina. These layers and films may be formed of an electrically insulating material containing, as a predominant component, at least one of silica, silica alumina, mullite, silicate glass, borate glass borosilicate glass, and phosphate glass.

(4) The metal oxide is not limited to oxides of bismuth vanadium such as bismuth vanadium oxide, and may be vanadium oxide, bismuth oxide, or a composite oxide of vanadium oxide and bismuth oxide.

(5) In order to finely adjust the catalytic performance of the selective reaction electrode layers 360 and 990 and/or improve their thermal stabilities, at least one of $WO_3$, $MoO_3$, $Nb_2O_5$, $Ta_2O_5$, MgO, CaO, SrO and BaO may be added to the metal oxide in an amount up to about 5 mol %.

(6) Instead of the metal oxide, the selective reaction layers 360 and 990 may be formed of a material containing palladium. In this case also, the gas selectivity for ammonia can be well secured.

(7) The shape of the insulating layers 340 and 380 described in Embodiments 1 to 3 is not limited to a strip-like shape, and the insulating layers 340 and 380 may be formed over the entire circumference of the solid electrolyte member 310. Meanwhile, the insulating films 950 and 970 described in Embodiment 4 may assume the form of a strip having a width corresponding to that of the lead 960.

(8) The detection electrode 335 and the detection lead 350 described in Embodiments 1 to 3 do not overlap. However, the detection electrode 335 may be disposed such that it overlaps the detection lead 350 in order to improve the reliability of electrical connection.

(9) Application of the ammonia gas sensor of the present invention is not limited to the exhaust gas system of an internal combustion engine, and the present invention can be applied to any other engine, apparatus or the like which generates an exhaust gas.

While the invention has been described in detail and with reference to specific embodiments thereof, it would be apparent to one skilled in the art that various changes and modifications can be made therein without departing from the spirit and scope thereof.

This application is based on Japanese Patent Application No. 2007-181575 filed Jul. 11, 2007 and Japanese Patent Application No. 2008-120858 filed May 7, 2008, the above-noted applications incorporated herein by reference in their entirety.

What is claimed is:

1. An ammonia gas sensor comprising:
   a solid electrolyte member which extends in an axial direction and contains zirconia as a predominant component;
   a detection portion provided on a front surface of the solid electrolyte member;
   a reference electrode provided on a back surface of the solid electrolyte member;
   a detection lead provided directly, or via another member, on the front surface of the solid electrolyte member so as to establish electrical connection between the detection portion and an external circuit, and
   an insulating portion provided at least on a surface of the detection lead or between the detection lead and the solid electrolyte member, wherein the detection portion includes a detection electrode formed of a noble metal, and a selective reaction layer formed of a metal oxide having selectivity for ammonia gas,
   wherein the detection electrode is provided directly, or via another member, on the solid electrolyte member; and
   the selective reaction layer is provided directly, or via another member, on the detection electrode, and
   wherein the insulating portion is formed on the surface of the detection lead, and includes a first insulating portion which extends in the axial direction onto the surface of the detection electrode to shield the detection lead from exposure to a gas under measurement through the detection electrode, wherein the first insulating portion extends to the detection electrode so as to be provided at an interface between the selective reaction layer and the detection electrode,
   wherein the metal oxide is vanadium oxide, bismuth oxide, or a composite oxide of vanadium oxide and bismuth oxide, and
   wherein the selective reaction layer overlaps the first insulating portion.

2. The ammonia gas sensor according to claim 1, wherein a length of the first insulating portion, as measured in the axial direction, is greater than a thickness of the detection electrode.

3. The ammonia gas sensor according to claim 1, wherein the insulating portion is provided between the detection lead and the solid electrolyte member, and further includes a second insulating portion extending in the axial direction between the detection electrode and the solid electrolyte member.

4. The ammonia gas sensor according to claim 3, wherein a length of the second insulating portion, as measured in the axial direction, is greater than a thickness of the detection electrode.

5. The ammonia gas sensor according to claim 4, wherein a length of the first insulating portion, as measured in the axial direction, is greater than the length of the second insulating portion.

6. The ammonia gas sensor according to claim 1, wherein the solid electrolyte member assumes the form of a tube having a bottom at a front end portion thereof;
   the reference electrode is formed on an inner surface of the solid electrolyte member;

the detection portion is provided on an outer surface of the front end of the solid electrolyte member; and the detection lead assumes the form of a strip and extends rearward in the axial direction from the detection portion.

7. The ammonia gas sensor according to claim 6, wherein the reference electrode and the detection lead face one another via the solid electrolyte member.

8. The ammonia gas sensor according to claim 6, comprising a heater disposed in the tubular solid electrolyte member so as to contact the reference electrode, and the position of contact between the heater and the reference electrode is located frontward of the insulating portion.

9. The ammonia gas sensor according to claim 8, wherein the heater includes a heating resistor disposed in a front end portion thereof and a heater lead extending rearward from the heating resistor, and the heating resistor is located frontward of the insulating layer.

10. The ammonia gas sensor according to claim 1, wherein the solid electrolyte member assumes the form of a plate extending in the axial direction;

the detection portion is provided on a front surface of a front end portion of the solid electrolyte member; and the detection lead assumes the form of a strip extending rearward in the axial direction from the detection portion.

11. The ammonia gas sensor according to claim 1, wherein the insulating portion contains, as a predominant component, one of alumina, silica, silica alumina, mullite, silicate glass, borate glass, borosilicate glass and phosphate glass.

12. The ammonia gas sensor according to claim 1, wherein the selective reaction layer covers the detection electrode such that the detection electrode is not exposed.

13. The ammonia gas sensor according to claim 1, wherein the detection electrode and the detection lead each independently contains one of gold and platinum as a predominant component.

14. An ammonia gas sensor comprising:

A solid electrolyte member which extends in an axial direction and contains zirconia as a predominant component;

A detection portion provided on a front surface of the solid electrolyte member;

A reference electrode provided on a back surface of the solid electrolyte member;

A detection lead provided direction, or via another member, on the front surface of the solid electrolyte member so as to establish electrical connection between the detection portion and an external circuit, and An insulating portion provided at least on a surface of the detection lead or between the detection lead and the solid electrolyte member, Wherein the detection portion includes a detection electrode formed of a noble metal, and a selective reaction layer formed of a metal oxide having selectivity for ammonia gas, Wherein the detection electrode is provided directly, or via another member, on the solid electrolyte member; and The selective reaction layer is provided directly, or via another member, on the detection electrode, and Wherein the insulating portion is provided between the detection lead and the solid electrolyte member, and includes a second insulating portion extending in the axial direction at an interface between the detection electrode and the solid electrolyte member, Wherein the metal oxide is vanadium oxide, bismuth oxide, or a composite oxide of vanadium oxide and bismuth oxide, and Wherein the selective reaction layer overlaps the second insulating portion so that a portion of the detection electrode is disposed between the selective reaction layer and the insulating portion, Wherein the insulating portion further comprises an additional insulating portion formed on the surface of the detection lead and extends onto the surface of the detection electrode to shield the detection lead from exposure to a gas under measurement through the detection electrode such that the selective reaction layer overlaps the additional insulating portion.

15. The ammonia gas sensor according to claim 14, wherein the selective reaction layer covers the detection electrode such that the detection electrode is not exposed.

16. The ammonia gas sensor according to claim 14, wherein the detection electrode and the detection lead each independently contains one of gold and platinum as a predominant component.

17. The ammonia gas sensor according to claim 16, wherein the detection electrode includes zirconia; and the detection lead includes alumina.

18. The ammonia gas sensor according to claim 14, wherein the selective reaction layer includes palladium in place of at least part of the metal oxide.

* * * * *